United States Patent
Matsumoto et al.

[11] Patent Number: 6,083,440
[45] Date of Patent: *Jul. 4, 2000

[54] METHOD OF MAKING AN OUTER CANNULA FOR AN INTRAVENOUS CANNULA AND A CANNULA MADE BY THE METHOD

[75] Inventors: Takashi Matsumoto, Kawasaki; Takahito Wakabayashi; Hiroshi Okada, both of Kusatsu, all of Japan

[73] Assignee: Nissho Corporation, Osaka-fu, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/766,663

[22] Filed: Dec. 4, 1996

[30] Foreign Application Priority Data

Dec. 4, 1995 [JP] Japan .................. 7-315202

[51] Int. Cl.$^7$ .................. B29C 57/00
[52] U.S. Cl. .................. 264/138; 264/296; 264/323; 425/393
[58] Field of Search .................. 264/138, 161, 264/296, 323, 320; 425/393

[56] References Cited

U.S. PATENT DOCUMENTS

| | | | |
|---|---|---|---|
| 4,404,159 | 9/1983 | McFarlane | 264/296 |
| 4,551,292 | 11/1985 | Fletcher et al. | 264/320 |
| 4,661,300 | 4/1987 | Daugherty | 264/320 |
| 4,961,809 | 10/1990 | Martin | 264/322 |
| 5,135,599 | 8/1992 | Martin et al. | 264/322 |
| 5,178,803 | 1/1993 | Tsuchida et al. | 264/296 |
| 5,360,330 | 11/1994 | Jensen et al. | 425/144 |
| 5,409,644 | 4/1995 | Martin et al. | 264/296 |
| 5,716,410 | 2/1998 | Wang et al. | 623/12 |

FOREIGN PATENT DOCUMENTS

| | | |
|---|---|---|
| 0 508 118 | 10/1992 | European Pat. Off. . |
| 63-270063 | 11/1988 | Japan . |

OTHER PUBLICATIONS

Patent Abstracts of Japan, Publication No. 62–270063, Publication Date: Nov. 8, 1988.

*Primary Examiner*—Jan H. Silbaugh
*Assistant Examiner*—Mark Eashoo
*Attorney, Agent, or Firm*—Kubovcik & Kubovcik

[57] ABSTRACT

A method for making an outer cannula of an intravenous cannula. An insert pin (3) is inserted into an outer cannula (1) having a hub (12) and a tube (11) made of a shape memory polyurethane resin and having an untreated distal end portion, until a tip end of the insert pin (3) reaches a position retracted from a distal end of the tube (11). While holding the position of the insert pin (3), the tube (11) with the insert pin (3) is forced into a cavity in a mold (4) heated to a temperature of 120° C. to 180° C. until the insertion of the tube into the cavity is obstructed. Subsequently, the insert pin (3) is moved within the tube (11) toward the extremity of the tube until the tip end of insert pin (3) reaches a first predetermined position in the mold (4). After maintaining the tube at the mold temperature until the tube is softened, the insert pin is further moved within the tube toward the extremity thereof and held in position for a certain period of time. The mold (4) is then cooled for a certain period of time. Then, the tube (11) is removed from the mold (4) together with insert pin (3), and subsequently the insert pin (3) is removed from the tube (11). Finally, the distal end portion of the tube (11) is cut to a desired length.

3 Claims, 6 Drawing Sheets

Fig.4a   Fig.4b
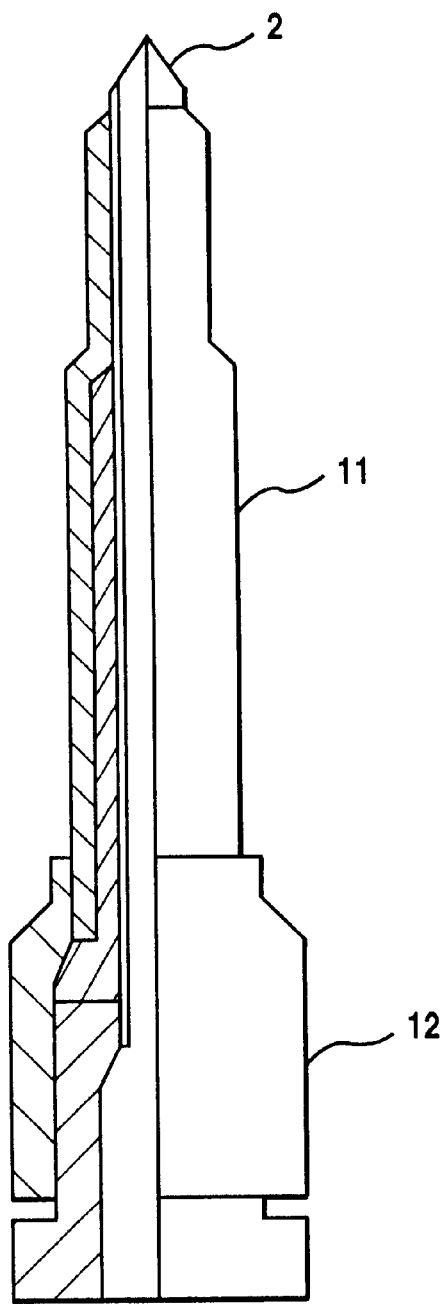
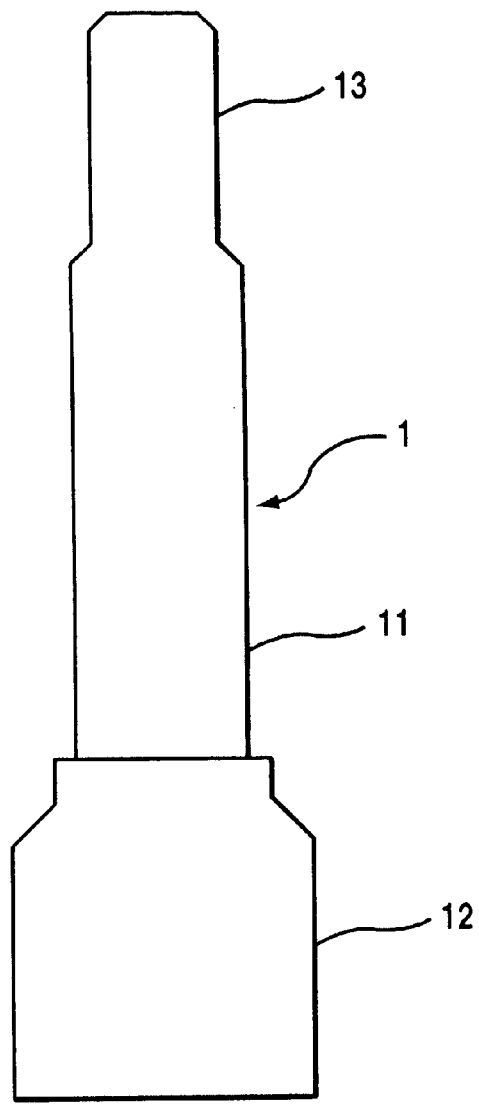

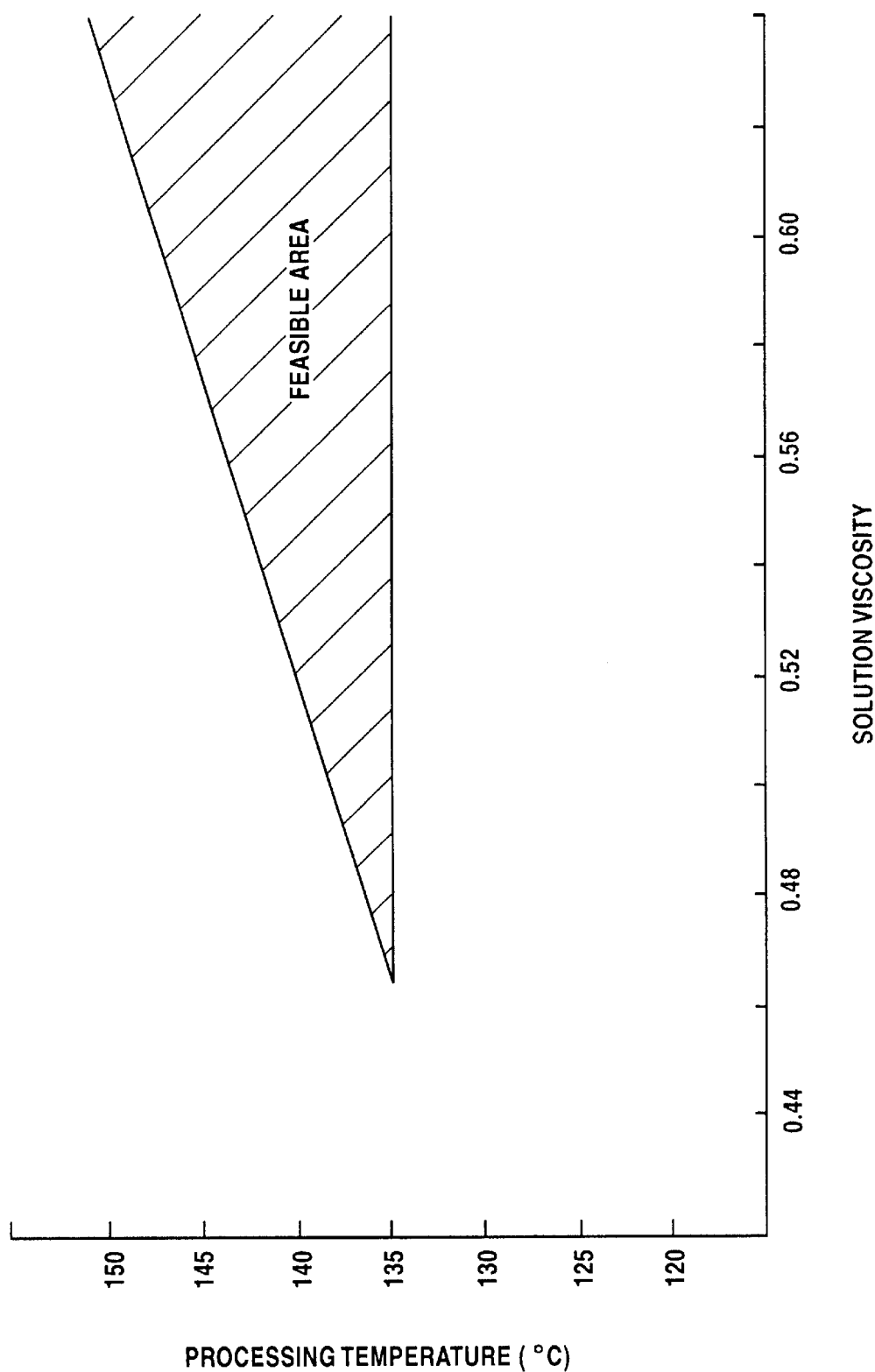

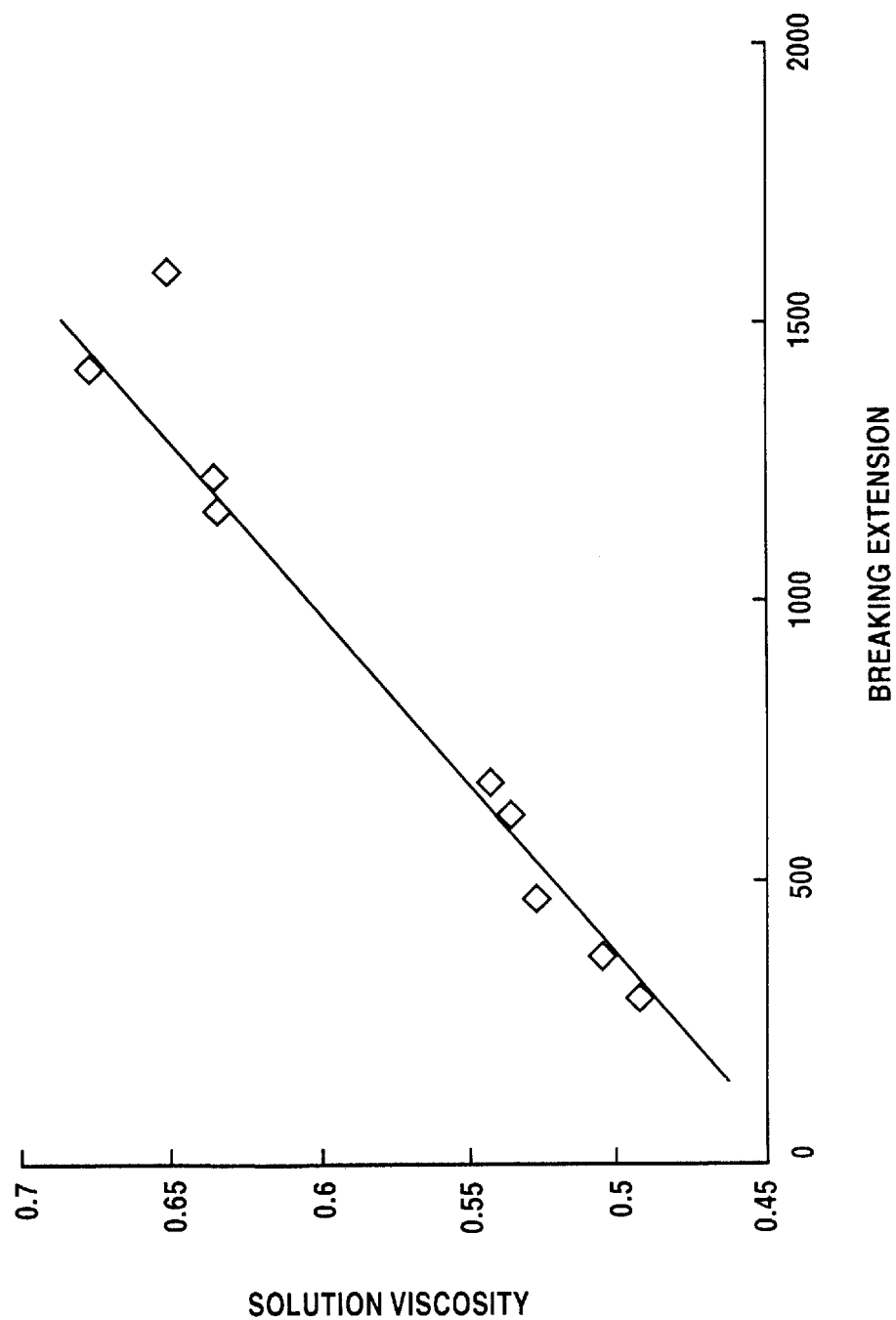

METHOD OF MAKING AN OUTER CANNULA FOR AN INTRAVENOUS CANNULA AND A CANNULA MADE BY THE METHOD

BACKGROUND OF THE INVENTION

1. Field of the Invention

The present invention relates to a method of making an outer cannula for an intravenous cannula wherein the end of a previously formed tube of a shape memory resin such as a polyurethane resin is formed in a mold.

2. Description of the Prior Art

A catheter (herein referred to as an "intravenous cannula") is widely used for transfusing blood or liquid medicines. The intravenous cannula is maintained in the blood vessel of a patient for a time necessary for medical treatment. Generally, an intravenous cannula comprises an outer cannula made of a thermoplastic resin and an inner cannula made of stainless steel. The inner cannula is removed from a patient, after having been inserted with the outer cannula into the patient. Subsequently, a blood transfusion set or infusion set or the like is connected with the outer cannula remaining in the patient's body.

The distal end of an outer cannula has a thin peripheral wall such that the difference in outside diameters between the outer cannula and the inner cannula is minimized for a smoother piercing of the skin of a patient. The materials used to form an outer cannula include polytetrafluoroethylene (PTFE), polyurethane, polyethylene and the like.

In some cases, an outer cannula with a thin end is injection molded in its entirety. In other cases, one end of a previously prepared thin tube is mechanically sharpened using a machining apparatus.

Prior art methods of forming the thin end of an outer cannula are somewhat disadvantageous, particularly when a shape memory polyurethane resin is used. It has been difficult for an injection molding process to produce a thin outer cannula in a rapid and efficient manner from such a resin. An outer cannula is likely to be damaged at its thin end when and after it is ejected from a mold. Also, it is not easy to insert a cannula into the outer cannula. A separate process must be used and an automatic production system is not possible. Thus, despite the use of expensive molds, a labor and time consuming operation has been necessary to handle a molded cannula. Inner cannulas which vary greatly in diameter will cause significant variations in engagement strength when fitted in the respective outer cannula. In addition, except for the hot runner type of mold, injection molds generally produce a significant amount of waste, causing a remarkable loss in material and further increasing manufacturing costs. On the other hand, the mechanical sharpening of ends of previously produced tubes will inevitably cause them to be electrostatically charged during the process so that dust and chips will stick to the outer surface of the tubes.

SUMMARY OF THE INVENTION

An object of the present invention is to provide a novel method of making an outer cannula of an intravenous cannula from a length of tube of a shape memory resin, such that the outer cannula has a thin distal end portion that reduces the penetration force of the cannula.

The present inventors tried at first to use a prior art method which they had developed and which is disclosed in Japanese Unexamined Patent Publication No. 63-270063. However, they found that the distal end of a shape memory polyurethane resin tube was highly susceptible to undesirable deformation if a mold was not operated at a proper temperature. In the prior art method, an insert pin is inserted in an axial bore of the tube. An end of the tube when heated and softened in a mold tends to elongate (producing an undesirable shape) when the tube together with the insert pin are removed from the mold. To avoid these problems the inventors have developed an improved method in which the mold is heated to a temperature within a range of about 120° C. to 180° C., and the tube heated together with the insert pin and forced into a desired shape is cooled before being removed from the mold together with the insert pin.

More specifically, the method according to the present invention comprises a first step of preparing an outer cannula having a hub and a tube having an untreated distal end portion and made of a shape memory polyurethane resin. An insert pin having a diameter smaller than an inside diameter of the tube is inserted into the tube until a tip end of the insert pin reaches a position retracted a predetermined distance from a distal end of the tube.

As a second step, while maintaining the position of the insert pin in the tube, the tube and insert pin are inserted into a cavity formed in a mold which is heated to a temperature of about 120° C. to 180° C. until the insertion of the tube into the cavity is obstructed by a region of the cavity having a diameter greater than the diameter of the insert pin and smaller than an outside diameter of the tube. The insert pin is then moved within the tube towards the extremity thereof until the tip end of the insert pin reaches a second predetermined position.

As a third step, the tube is maintained at 120° C. to 180° C. until the tube is softened. The insert pin is then moved further within the tube towards the extremity thereof until the tip end of the insert pin reaches a third predetermined position. The insert pin is then held in place for a certain period of time.

As a fourth step, the mold is cooled.

As a fifth step, the cooled tube is removed from the mold together with the insert pin inserted therein.

As a sixth step, the insert pin is removed from the tube.

As a seventh step, the distal end portion of the tube is cut to a desired length.

Preferably, the outer cannula for an intravenous cannula manufactured by the method as summarized above has a wall thickness of 0.05 mm or less at its distal end portion.

The mold used in the method of the present invention preferably has a cavity comprising a first tapered region located at the outermost portion of the mold, a second tapered region adjacent the first tapered region and a straight region adjacent the second tapered region and located in the innermost portion of the mold. The first tapered region, which extends from a tube insertion opening of the mold into the mold, is tapered gently at a large angle, the tube insertion opening having a diameter larger than the outside diameter of the tube. The second tapered region is tapered at a smaller angle than that of the first tapered region. The straight region has a diameter greater than the diameter of the insert pin but smaller than the outside diameter of the tube.

An outer cannula is preferably produced using this mold under conditions defined by the following two equations:

$$0.02 \leq Dc - Dm \leq 0.1 \qquad \text{(i)}$$

$$1.2t \leq Dt - Dc \leq 3t \qquad \text{(ii)}$$

wherein

Dt=outside diameter of the tube, t=desired thickness of the tube at its distal end, Dm=diameter of the insert pin, and Dc=inside diameter of the straight region of the mold, with all the dimensions being in millimeters.

BRIEF DESCRIPTION OF THE DRAWINGS

FIG. 4a is a front elevation of an intravenous cannula comprising the outer cannula and an inner cannula, both partly shown in cross section;

FIG. 4b is a front elevation of the outer cannula;

FIG. 5 is a graph showing a relationship observed between the temperature at which a raw tube is processed in the method of the present invention and the solution viscosity of a shape memory polyurethane resin forming the raw tube, wherein an area showing preferable combinations of these parameters is denoted in the graph; and FIG. 6 is another graph showing a relationship between the solution viscosity of said shape memory polyurethane resin and the breaking extension of said tube.

DETAILED DESCRIPTION OF THE PREFERRED EMBODIMENTS

Figure 1:
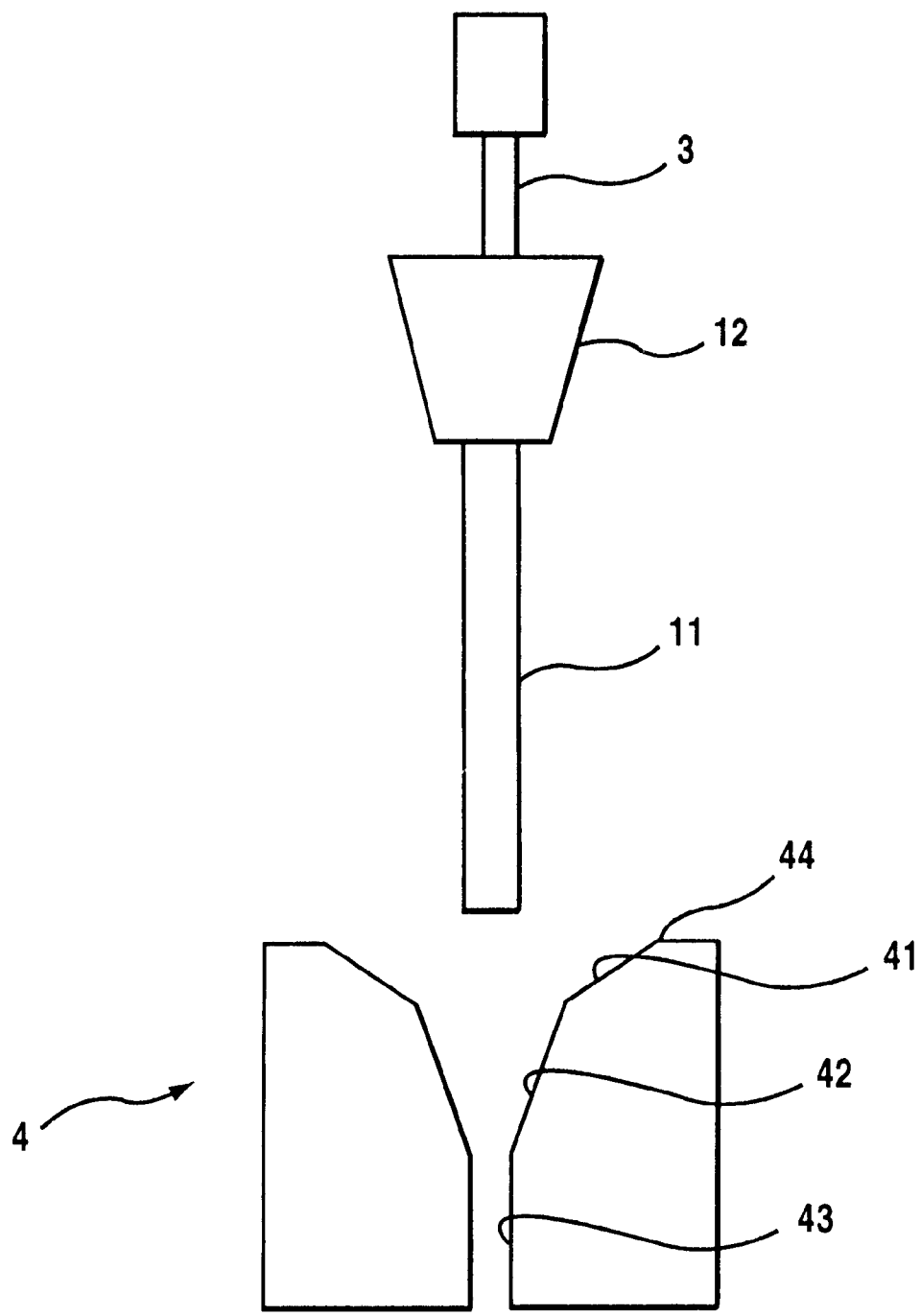
FIG. 1 shows an outer cannula starting material and a mold used in the method of the present invention.

A preferred embodiment of the present invention is described below with reference to the drawings.

As can be seen by referring to FIGS. 4a and 4b, an outer cannula 1 of an intravenous cannula comprises a tube 11 and a hub 12. A finished distal end portion 13 of this tube will have a peripheral wall whose thickness is 0.05 mm or less. Attached to a proximal end of the tube 11 is a hub 12 made of a plastic such as polypropylene, polyethylene or polycarbonate. The intravenous cannula is composed of the outer cannula 1 and an inner cannula 2 inserted therein. After this intravenous cannula 1 is used to pierce a patient's skin, the inner cannula 2 is withdrawn so that a catheter or a guide wire (not shown) can be inserted through the outer cannula 1.

An end of a raw starting tube for the outer cannula is processed according to the present method so as to provide the outer cannula 1 with the finished distal end portion. In the present method, the conditions of molding such as the configuration of the molding cavity, diameter of an insert pin 3, heating temperature, heating time, cooling temperature, cooling time and the like are appropriately controlled. Thus, the distal end portion can be finished to an accurate shape in an invariable and reliable manner.

Figure 2:
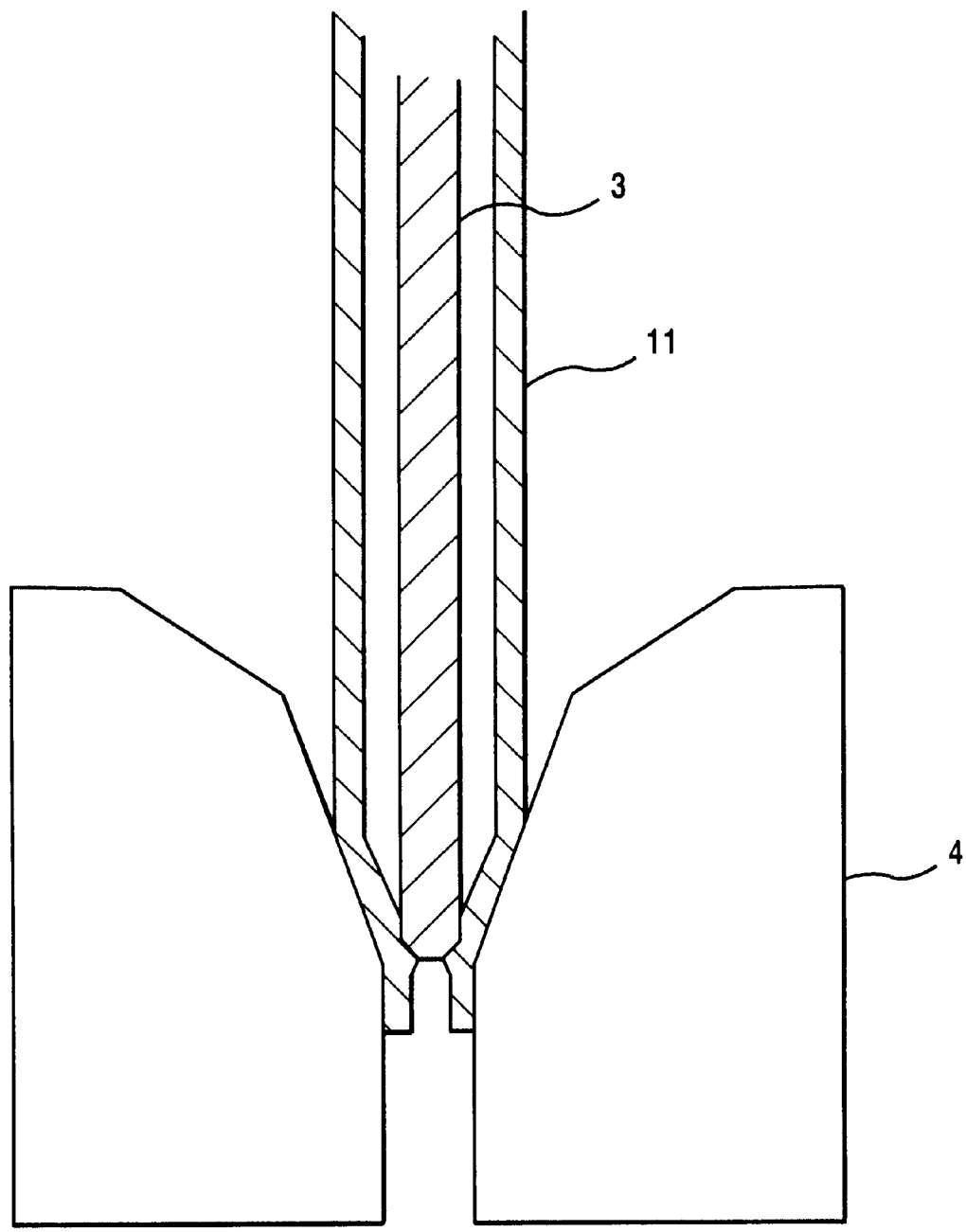
FIG. 2 illustrates a step in the method of the present invention, with some parts being shown in cross section.
Figure 3:
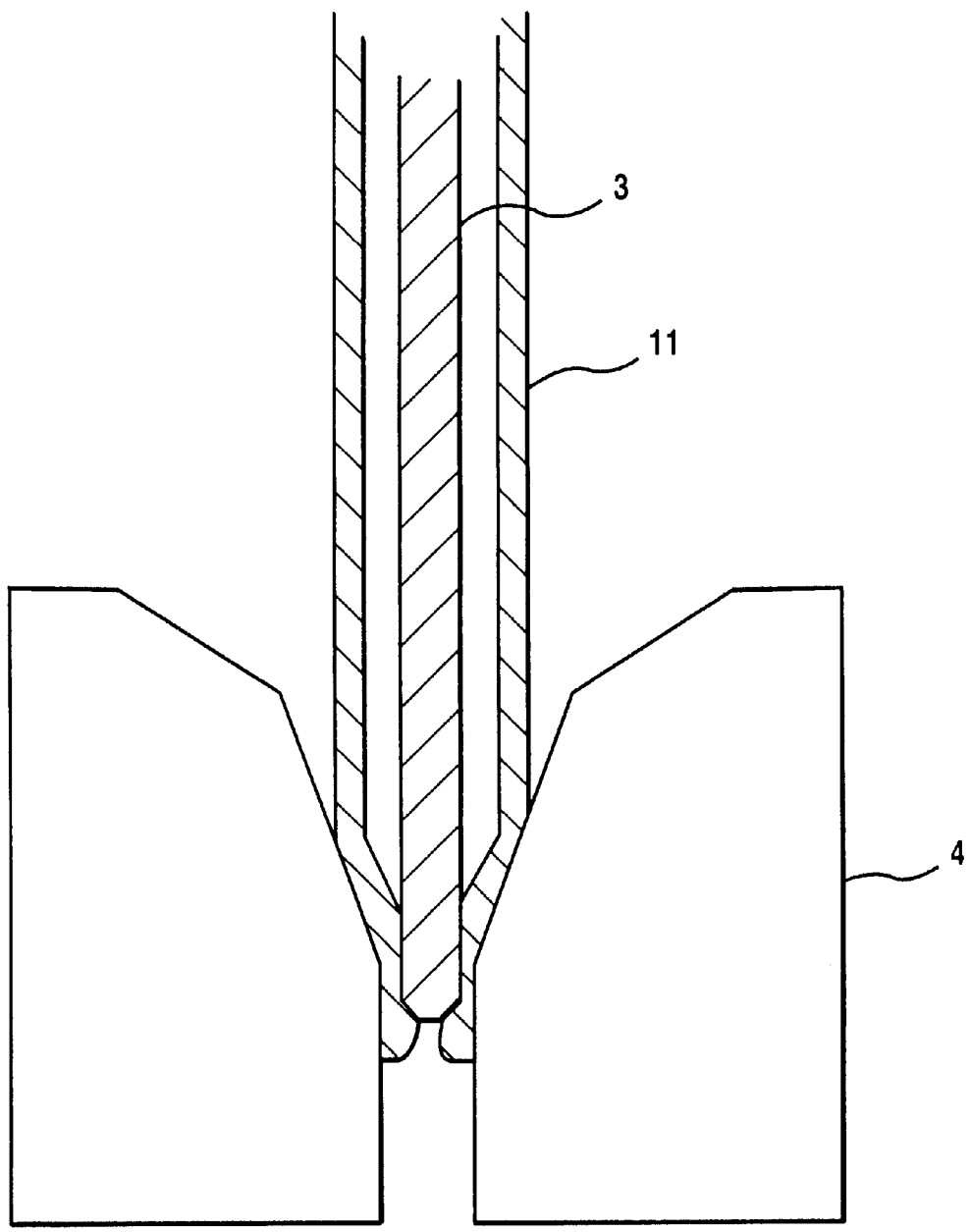
FIG. 3 similarly illustrates another step in the method of the present invention, with the parts also shown in cross section.

The method of the present invention will now be described in detail, referring in particular to FIGS. 1 to 3.

In a first step, an outer cannula 1 consisting substantially of a tube 11 made of a shape memory polyurethane resin and a hub 12 is prepared. The tube 11 has an untreated distal end portion. An insert pin 3 having a diameter smaller than an inner diameter of the tube is inserted into the tube 11 such that the tip end of the insert pin 3 reaches a position retracted a distance remote from a distal end of the tube 11. The insert pin 3 has a diameter considerably smaller than the inner diameter of the tube 11. A device (not shown) is used to automatically insert the insert pin 3 into the tube 11. The insert pin 3 is usually inserted into a position retracted a distance 4–6 mm and, more preferably, about 5 mm from the distal end of the tube 11.

A mold 4 as used in the method of the present invention is illustrated in FIG. 1, and has a cavity composed of a first tapered region 41, a second tapered region 42 and a straight region 43.

The first tapered region 41 has a cavity considerably greater in diameter than the outer diameter of the tube 11, and has a tube insertion opening 44 wide enough to smoothly receive said tube. The angle at which the first tapered region 41 is tapered is preferably about 30° to 60° relative to the axis of the mold cavity, although the angle is not limited thereto.

The second tapered region 42 is gently tapered at a smaller angle than the first tapered region 41 so as to continue from the first tapered region 41 to the straight region 43. The diameter of the second tapered region 42 at its boundary with the first tapered region 41 is greater than the outer diameter of the tube 11, but is smaller at its boundary with the straight region 43 than the outer diameter of the tube 11. The tapering angle of the second tapered region 42 is preferably 4° to 15°. If this angle is significantly greater than 15°, then the outer cannula 1 prepared using the mold will have a higher penetration force so that patients will experience greater pain when their veins are pierced with such a cannula. If, on the other hand, the angle is noticeably smaller than 4°, then the taper of the tube 11 will extend an excessive distance, thereby making it difficult to handle because inner cannula 2 will firmly engage the outer cannula 1. Such an elongated distal end portion 13 of outer cannula 1 will also be excessively thin and will probably be bent or split when used to pierce the patient's skin.

The inside diameter of the straight region 43 is smaller than the outer diameter of the tube 11 but greater than the diameter of the insert pin 3. The length of region 43 is determined depending on the size of outer cannula 1. The mold is prepared out of a column of material, 4 mm of diameter and 10 mm of height. If diameters of the outer cannula differ, relative lengths of the tapered region and straight region will differ because the same size of column is used always. Specifically, the diameters of the second tapered region and the straight region are controlled by the diameter of the outer cannula 1 because the same size (length) mold is always used. If the diameter of the outer cannula is bigger, the length of the tapered region is longer and the length of the straight region 43 is shorter. On the other hand, if the diameter of the outer cannula 1 is smaller, the length of the tapered region is shorter and the length of the straight region 43 is longer.

In the second step, while axially holding the hub 12 and insert pin 3 so as not to move the insert pin 3 within the tube 11, the tube 11 having the insert pin 3 that was inserted therein the first step is inserted into the cavity formed in the mold 4, which has been preheated to a temperature of about 120° C. to 180° C., until the insertion of the tube 11 into the cavity is obstructed by the second tapered region 42 where the diameter of the cavity is greater than the diameter of the insert pin but is smaller than the outer diameter of the tube 11. Then as illustrated in FIG. 2, the insert pin 3 is moved within the tube 11 towards the extremity thereof until the tip end of insert pin 3 reaches a predetermined position of the mold 4. The position to which the tip end of the insert pin 3 is moved depends on the diameter of the outer cannula 1.

The insert pin 3 is usually moved to a position retracted 0.5–2.0 mm from the point where the second tapered region 42 ends and the straight region 43 begins.

If the mold 4 is preheated to a temperature less than 120° C., then the distal end portion of an outer cannula 1 of a finished product (i.e., an intravenous cannula) will undesirably expand and lose its finished shape when sterilizing the product at an elevated temperature. If the mold 4 is preheated to a temperature greater than 180° C., then fine corrugations will appear on the inside periphery of the distal end portion 13 of tube 11, or its tapered portion will collapse or otherwise be damaged.

In the third step, the tube 11 is held at the predetermined position for 0.5–1 second until the tube is softened. Subsequently the insert pin 3 is further moved within the tube towards the extremity thereof until the tip end of the insert pin 3 reaches a second predetermined position of the mold 4, while holding the hub 12, thereby forcing the resin into the straight region 43. The second predetermined position of the tip end of the insert pin 3 also depends on the diameter of the outer cannula 1 and is usually at the point where the second tapered region 42 ends and the straight region 43 begins or is up to about 1 mm inside the straight region 43. This position is maintained for 5–10 seconds to fix the shape of the distal end of the outer cannula 11.

In the fourth step, the mold 4 is cooled until the temperature is lower than the glass transition temperature of the shape memory polyurethane resin (about 35° C.–38° C.). Preferably the mold 4 is cooled down by air of about 20° C. for a period of 5 seconds.

In the fifth step the tube 11 is removed from the mold 4 together with the insert pin 3 inserted therein.

In the sixth step, the insert pin 3 is pulled out of the tube.

In the seventh step, the distal end portion 13 of the tube is cut to a predetermined length.

Preferably, the materials and mold 4 for forming the distal end of outer cannula 1 have the dimensions defined by the following two equations:

$$0.02 \leq Dc-Dm \leq 0.1 \quad \text{(i)}$$

$$1.2t \leq Dt-Dc \leq 3t \quad \text{(ii)}$$

wherein

Dt=outside diameter of the tube 11, t=desired wall thickness of the tube 11 at its distal end, Dm=diameter of the insert pin, and Dc=inside diameter of the straight region 43 of the mold, with all the dimensions being in millimeters.

If the difference "Dc–Dm" in equation (i) is greater than 0.1, the outer cannula 1 will exert an undesirably strong penetration force when piercing the skin of a patient. However, a difference smaller than 0.02 will possibly cause the tube to be broken, and even if the process can be completed, the outer cannula 1 will tend in use to be bent or split when piercing the skin.

If the other difference "Dt–Dc" in equation (ii) is greater than 3t, the tube 11 of outer cannula 1 will be excessively drawn or constricted in its outside diameter and thickness, thereby causing defects in the product. A longer heating time can be used to avoid this problem but will raise production costs and lower manufacturing efficiency. When this difference "Dt–Dc" is reduced below 1.2t, constriction of the tube wall will be insufficient, failing to provide a properly thinned distal end of said tube 11.

The shape memory polyurethane resin used in the method of the present invention has a molecular weight of 40,000–100,000.

In the preferred embodiment discussed above, the shape memory polyurethane resin used is a product of Mitsubishi Heavy Industries Co., Ltd. This resin "MM4510", which is a polyester type polyurethane, was tested to determine the relationship between its solution viscosity and the processing temperature as shown in FIG. 5, and the relationship between said viscosity and the breaking extension of products as shown in FIG. 6. The solution viscosity was determined by dissolving the polyurethane resin in dimethyl acetamide to form a 0.3 g/dl dimethyl acetamide solution. Logarithmic viscosity is measured under 30° C. of atmospheric temperature by an Oswald viscometer. The following formula is used to determine the logarithmic viscosity η:

$$\eta_{inh} = ln(t/t_o)/c,$$

where t: dropping time (seconds of 0.3 g/dl dimethyl acetamide solution of the resin $t_o$: dropping time of dimethyl acetamide (solvent)

c: concentration of solution (g/dl).

The breaking extension is measured under 110±0.5° C. of atmospheric temperature, 12.5 mm of chuck distance and 500 mm/min of rate of pulling according to ASTM D638-91. As will be seen in these figures, it is preferred that the viscosity is 0.47 or higher and the breaking extension is 500% or more at 110° C.

It will now be apparent that the present method is useful in the manufacture of an outer cannula of an intravenous cannula that has an accurate shape of the distal end portion and that produces a low penetration force to reduce the pain of piercing the skin.

What we claim is:

1. A method of making an outer cannula for an intravenous cannula, the method comprising the steps of:

providing a mold having a cavity comprising a first tapered region located at the outermost portion of the mold, a second tapered region adjacent the first tapered region and a straight region adjacent the second tapered portion and located in the innermost portion of the mold, the first tapered region continuing from a tube insertion opening of the mold and being tapered gently at a large angle, wherein the insertion opening is of a diameter larger than the outside diameter of the tube, the second tapered region being tapered at a smaller angle than that of the first tapered region, and the straight region having a diameter greater than the diameter of the insert pin but smaller than that of the tube;

preparing an outer cannula having a hub and a tube, wherein the tube is made of a shape memory polyurethane resin;

inserting an insert pin having a diameter smaller than an inside diameter of the tube into the tube until a tip end of the insert pin reaches a first predetermined position retracted from an extremity of a distal end of the tube;

preheating said mold to a temperature of about 120° C. to 180° C.;

while maintaining said first predetermined position of the insert pin in said tube, inserting the tube and insert pin into said cavity in said preheated mold until the inserting of the tube into the cavity is obstructed by a portion of said second tapered region of the cavity having a diameter greater than the diameter of the insert pin but smaller than an outside diameter of said tube, and subsequently moving the insert pin within the tube towards the extremity thereof until the tip end of the insert pin reaches a second predetermined position in the mold cavity;

maintaining the tube at 120° C. to 180° C. for a period of time to soften the tube and thereafter, while holding said hub of the outer cannula, moving the insert pin further within the tube towards the extremity thereof until the tip end of the insert pin reaches a third predetermined position in the mold cavity to force the tube into said straight region of the mold and form a distal end portion of said cannula therein, and holding the insert pin in place for a predetermined period of time;

cooling the mold below the glass transition temperature of the resin;

after cooling the mold and thereby the tube, removing the tube from the mold together with the insert pin inserted therein;

removing the insert pin from the tube; and cutting the distal end portion of the cannula to a desired length.

2. The method as defined in claim 1, wherein the shape memory polyurethane resin has a solution viscosity of 0.47 or higher and a breaking extension of 500% or more at 110° C.

3. The method as defined in claim 1, wherein the tube, insert pin and mold satisfy equations (i) and (ii):

$$0.02 \leq Dc-Dm \leq 0.1 \quad \text{(i)}$$

$$1.2t \leq Dt-Dc \leq 3t \quad \text{(ii)}$$

wherein:

Dt=outside diameter of the tube in millimeters, t=desired wall thickness of the distal end of the tube in millimeters, Dm=diameter of the insert pin in millimeters, and Dc=inside diameter of the straight region of the mold in millimeters.

* * * * *